(12) United States Patent
Delzer

(10) Patent No.: US 7,098,389 B2
(45) Date of Patent: Aug. 29, 2006

(54) INBRED MAIZE LINE NP2315

(75) Inventor: Brent Delzer, Janesville, WI (US)

(73) Assignee: Syngenta Participations AG, Basel (CH)

( * ) Notice: Subject to any disclaimer, the term of this patent is extended or adjusted under 35 U.S.C. 154(b) by 363 days.

(21) Appl. No.: 10/345,572

(22) Filed: Jan. 16, 2003

(65) Prior Publication Data

US 2004/0143866 A1 Jul. 22, 2004

(51) Int. Cl.
*A01H 1/00* (2006.01)
*A01H 5/00* (2006.01)
*A01H 5/10* (2006.01)
*C12N 15/09* (2006.01)

(52) U.S. Cl. .................. 800/320.1; 800/260; 800/265; 800/279; 800/278; 800/302; 800/301; 800/303; 435/412; 435/430.1; 435/424

(58) Field of Classification Search ............... 800/260, 800/265, 320.1, 295, 298, 278, 279, 301, 800/302, 303; 435/412, 424, 430.1
See application file for complete search history.

(56) References Cited

U.S. PATENT DOCUMENTS 5,523,520 A * 6/1996 Hunsperger et al. ........ 800/260
6,723,901 B1 * 4/2004 Perry ...................... 800/320.1

OTHER PUBLICATIONS

Kraft et al . Theor. Appl. Genet. 2000, vol. 101, pp. 323-326.*
Eshed et al. Genetics, vol. 143, pp1807-1817, 1996.*

* cited by examiner

*Primary Examiner*—Medina A. Ibrahim
(74) *Attorney, Agent, or Firm*—Bruce Vrana

(57) ABSTRACT

The invention relates to an inbred maize line, designated NP2315, to the seeds of inbred maize line NP2315, to the plants of inbred maize line NP2315, and to methods for producing a maize plant by crossing plants of maize inbred line NP2315 with itself or with another maize plant. The invention also relates to maize plants of inbred line NP2315 containing a transgene produced by transforming said plants with said transgene.

16 Claims, No Drawings

US 7,098,389 B2

INBRED MAIZE LINE NP2315

FIELD OF THE INVENTION

This invention is in the field of maize breeding, specifically relating to an inbred maize line designated NP2315.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male) and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile maize and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511, the disclosures of which are specifically incorporated herein by reference. There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (EPO 89/3010153.8 and WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904, which is incorporated herein by reference). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc.

Recurrent selection breeding can be used to improve populations of either self or cross-pollinating crops. Recurrent selection can be used to transfer a specific desirable trait from one inbred or source to an inbred that lacks the trait. This can be accomplished, for example, by first a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is, then selfed to give pure breeding progeny for the gene(s) being transferred. A hybrid developed from inbreds containing the transferred gene(s) is essentially the same as a hybrid developed form the same inbreds without the transferred genes. As the varieties developed using recurrent selection breeding contain almost all of the characteristics of the recurrent parent, selecting a superior recurrent parent is desirable.

A single cross maize hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

The development of a maize hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). Much of the hybrid vigor exhibited by F1 hybrids is lost in the next generation (F2). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed. Once the seed is planted, it is possible to identify and select these self-pollinated plants. These self-pollinated plants will be genetically equivalent to the female inbred line used to produce the hybrid. Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of A typical Plants in Hybrid Maize Seed by Postcontrol and Electrophoresis" Sarca, V. et al., Probleme de Genetica Teoritca si Aplicata Vol. 20 (1) p. 29–42.

As is readily apparent to one skilled in the art, the foregoing describes only two of the various ways by which the inbred can be obtained by those looking to use the germplasm. Other means are available, and the above examples are illustrative only.

Maize is an important and valuable field crop. Thus, a continuing goal of plant breeders is to develop high-yielding maize hybrids that are agronomically sound based on stable inbred lines. The reasons for this goal are obvious: to maximize the amount of grain produced with the inputs used and minimize susceptibility of the crop to pests and environmental stresses. To accomplish this goal, the maize breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. The probability of selecting any one individual with a specific genotype from a breeding cross is infinitesimal due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder. Thus, even if the entire genotypes of the parents of the breeding cross were characterized and a desired genotype known, only a few, if any, individuals having the desired genotype may be found in a large segregating F2 population. Typically, however, neither the genotypes of the breeding cross parents nor the desired genotype to be selected is known in any detail. In addition, it is not known how the desired genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents, as the breeder is unable to direct how the genomes combine or how they will interact with the environmental conditions. This unpredictability results in the expenditure of large amounts of research resources in the development of a superior new maize inbred line.

SUMMARY OF THE INVENTION

According to the invention, there is provided a novel inbred maize line, designated NP2315, having excellent Eye Spot and Northern Leaf Blight resistance relative to A619, a relative maturity of approximately 95–105 days based on the Comparative Relative Maturity Rating System for harvest moisture of grain, good Northern Corn Leaf Blight and Helminthosporium Leaf Blight resistance relative to A619, pale purple silk ends 3 days after emergence, and adapted to the Northern Cornbelt regions of the United States. This invention relates to the seeds of inbred maize line NP2315, to the plants of inbred maize line NP2315, to descendants of NP2315, and to methods for producing a maize plant by crossing the inbred line NP2315 with itself or another maize line. This invention further relates to hybrid maize seeds and plants produced by crossing the inbred line NP2315 with another maize line.

The invention is also directed to inbred maize line NP2315 into which one or more specific, single gene traits, for example transgenes, have been transformed and/or introgressed.

The invention is also directed to a NP2315-derived maize plant, or parts thereof, wherein at least one ancestor of the NP2315-derived maize plant is the inbred maize line NP2315, wherein the NP2315-derived maize plant expresses a combination of at least two NP2315 traits selected from the group consisting of: a relative maturity of approximately 95–105 days based on the Comparative Relative Maturity Rating System for harvest moisture of grain, good Northern Corn Blight resistance and Helminthosporium Leaf Blight resistance relative to A619, pale purples silk ends 3 days after emergence, and adapted to the Northern Cornbelt regions of the United States.

DETAILED DESCRIPTION OF THE INVENTION

Inbred maize lines are typically developed for use in the production of hybrid maize lines. Inbred maize lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Some of the most widely used of these laboratory techniques are Isozyme Electrophoresis and RFLPs as discussed in Lee, M., "Inbred Lines of Maize and Their Molecular Markers," The Maize Handbook, (Springer-Verlag, New York, Inc. 1994, at 423–432). Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless. Maize RFLP linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90. This study used 101 RFLP markers to analyze the patterns of 2 to 3 different deposits each of five different inbred lines. The inbred lines had been selfed from 9 to 12 times before being adopted into 2 to 3 different breeding programs. It was results from these 2 to 3 different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0–2% residual heterozygosity. Although this was a relatively small study, it can be seen using RFLPs that the lines had been highly homozygous prior to the separate strain maintenance.

The production of hybrid maize lines typically comprises planting in pollinating proximity seeds of, for example, inbred maize line NP2315 and of a different inbred parent maize plant, cultivating the seeds of inbred maize line NP2315 and of said different inbred parent maize plant into plants that bear flowers, emasculating the male flowers of inbred maize line NP2315 or the male flowers of said different inbred parent maize plant to produce an emasculated maize plant, allowing cross-pollination to occur between inbred maize line NP2315 and said different inbred parent maize plant and harvesting seeds produced on said emasculated maize plant. The harvested seed are grown to produce hybrid maize plants.

Inbred maize line NP2315 can be crossed to inbred maize lines of various heterotic group (see e.g. Hallauer et al. (1988) in Corn and Corn Improvement, Sprague et al, eds, chapter 8, pages 463–564) for the production of hybrid maize lines.

TABLE I

VARIETY DESCRIPTION INFORMATION
Inbred maize line NP2315 is compared to inbred A619

| | INBRED NP2315 | | | INBRED A619 | | |
|---|---|---|---|---|---|---|
| MATURITY | Days | Heat Units | | Days | Heat Units | |
| From emergence to 50% of plants in silk | 070 | 1385.5 | | 068 | 1319.9 | |
| From emergence to 50% of plants in pollen | 069 | 1348.1 | | 066 | 1276.3 | |
| From 10% to 90% pollen shed | 003 | 0152.6 | | 003 | 0115.3 | |
| PLANT | | Std Dev | Sample Size | | Std Dev | Sample Size |
| cm Plant Height (to tassel tip) | 159.5 | 7.0 | 8 | 182.3 | 19.9 | 8 |
| cm Ear Height (to base of top ear node) | 053.1 | 6.6 | 8 | 044.3 | 6.2 | 8 |

TABLE I-continued

VARIETY DESCRIPTION INFORMATION
Inbred maize line NP2315 is compared to inbred A619

| | INBRED NP2315 | | | INBRED A619 | | |
|---|---|---|---|---|---|---|
| cm Length of Top Ear Internodenode | 13.0 | 1.2 | 7 | 14.6 | 0.9 | 7 |
| Average Number of Tillers | 0 | 0 | 7 | 0.1 | 0.3 | 7 |
| Average Number of Ears per Stalk | 1.4 | 0.6 | 6 | 1.2 | 0.3 | 6 |
| Anthocyanin of Brace Roots: 1 = Absent 2 = Faint 3 = Moderate 4 = Dark | 3 | | | 2 | | |
| LEAF | | Std Dev | Sample Size | | Std Dev | Sample Size |
| Cm Width of Ear Node Leaf | 010.4 | 0.9 | 8 | 008.9 | 0.6 | 8 |
| cm Length of Ear Node Leaf | 061.6 | 5.1 | 8 | 068.2 | 8.2 | 8 |
| Number of leaves above top ear | 5 | 0.7 | 8 | 6 | 0.4 | 8 |
| degrees Leaf Angle (measure from 2nd leaf above ear at anthesis to stalk above leaf) | 44 | 17.0 | 8 | 46 | 22.2 | 7 |
| Leaf Color | 02 | (Munsell code 5GY 5/4) | | 03 | (Munsell code 5GY 4/4) | |
| Leaf Sheath Pubescence (Rate on scale from 1 = none to 9 = like peach fuzz) | 6 | | | 2 | | |
| Marginal Waves (Rate on scale from 1 = none to 9 = many) | 5 | | | 6 | | |
| Longitudinal Creases (Rate on scale from 1 = none to 9 = many) | 6 | | | 5 | | |
| TASSEL | | | | | | |
| Number of Primary Lateral Branches | 7 | 3.9 | 8 | 6 | 2.7 | 8 |
| Branch Angle from Central Spike | 37 | 12.8 | 7 | 56 | 9.5 | 5 |
| Cm Tassel Length (from top leaf collar to tassel tip) | 40.7 | 3.7 | 7 | 41.4 | 5.0 | 7 |
| Pollen Shed (Rate on scale from 0 = male sterile to 9 = heavy shed) | 5 | | | 6 | | |
| Anther Color | 05 | (Munsell code 5GY 8/6) | | 05 | (Munsell code 2.5GY 8/6) | |
| Glume Color | 02 | (Munsell code 5GY 5/6) | | 03 | (Munsell code 7.5GY 5/6) | |
| Bar Glumes (Glume Bands): 1 = Absent 2 = Present | 2 | | | 2 | | |
| EAR (Unhusked Data) | | | | | | |
| Silk Color (3 days after emergence) | 26 | (Munsell code) | | 05 | (Munsell code 2.5GY 8/6) | |
| Fresh Husk Color(25 days after 50% silking) | 05 | (Munsell code 5GY 7/6) | | 05 | (Munsell code 5GY 8/6) | |
| Dry Husk Color (65 days after 50% silking) | 22 | (Munsell code 2.5Y 8/4) | | 22 | (Munsell code 2.5Y 8/4) | |
| Position of Ear at Dry Husk Stage: 1 = Upright 2 = Horizontal 3 = Pendent | 3 | | | 1 | | |
| Husk Tightness (Rate on scale from 1 = very loose to 9 = very tight) | 7 | | | 6 | | |
| Husk Extension (at harvest): 1 = Short (ears exposed) 2 = Medium (<8 cm) 3 = Long (8–10 cm beyond ear tip) 4 = Very long (>10 cm) | 2 | | | 2 | | |
| EAR (Husked Ear Data) | | Std Dev | Sample Size | | Std Dev | Sample Size |
| Cm Ear Length | 13.6 | 0.7 | 8 | 13.7 | 1.6 | 8 |
| mm Ear Diameter at mid-point | 37.8 | 1.1 | 8 | 44.9 | 2.0 | 7 |
| gm Ear Weight | 95.9 | 27.3 | 8 | 115.0 | 20.4 | 7 |
| Number of Kernel Rows | 16 | 0.8 | 8 | 15 | 0.2 | 7 |
| Kernel Rows: 1 = Indistinct 2 = Distinct | 2 | | | 2 | | |
| Row Alignment: 1 = Straight 2 = Slightly Curved 3 = Spiral | 1 | | | 1 | | |
| cm Shank Length | 10.9 | 1.7 | 7 | 11.4 | 3.4 | 7 |
| Ear Taper: 1 = Slight 2 = Average 3 = Extreme | 2 | | | 2 | | |
| KERNEL (Dried) | | Std Dev | Sample Size | | Std Dev | Sample Size |
| mm Kernel Length | 09.7 | 0.6 | 7 | 10.8 | 0.9 | 7 |
| mm Kernel Width | 7.4 | 0.5 | 7 | 08.6 | 0.5 | 7 |
| mm Kernel Thickness | 05.2 | 0.5 | 7 | 04.4 | 1.1 | 7 |
| % Round Kernels (Shape Grade) | 57.0 | 4.9 | 6 | 38.8 | 24.7 | 6 |
| Aleurone Color Pattern: 1 = Homozygous 2 = Segregating | 1 | | | 1 | | |
| Aleurone Color | 19 | (Munsell code) | | 19 | (Munsell code) | |

TABLE I-continued

VARIETY DESCRIPTION INFORMATION
Inbred maize line NP2315 is compared to inbred A619

| | INBRED NP2315 | | | INBRED A619 | | |
|---|---|---|---|---|---|---|
| Hard Endosperm Color | 06 | (Munsell code 2.5Y 8/10) | | 06 | (Munsell code 2.5Y 8/8) | |
| Endosperm Type:<br>1 = Sweet (su1) 2 = Extra Sweet (sh2)<br>3 = Normal Starch | 3 | | | 3 | | |
| Gm Weight per 100 Kernels (unsized sample) | 27.7 | 1.5 | 7 | 30.4 | 2.1 | 7 |
| COB | | Std Dev | Sample Size | | Std Dev | Sample Size |
| mm Cob Diameter at mid-point | 23.5 | 1.6 | 8 | 26.5 | 0.8 | 8 |
| Cob Color | 19 | (Munsell code ) | | 19 | (Munsell code) | |
| DISEASE RESISTANCE (1 = most susceptible to 9 = most resistant) | | | | | | |
| Eye Spot (Kabatiella zeae) | 8 | | | 5 | | |
| Northern Leaf Blight | 8 | Mixed Inoc. | | 5 | Mixed Inoc. | |
| Gray Leaf Spot | | | | | | |
| Common Rust | | | | | | |
| Helminthosporium Leaf Blight | 8 | | | 5 | | |
| INSECT RESISTANCE(Rate from 1 = most susceptible to 9 = most resistant) | | | | | | |
| European Corn Borer(Osstrinia nubilalis) | | | | | | |
| 1st Generation (Typically Whorl Leaf Feeding) | | | | | | |
| 2nd Generation Corn Borer | | | | | | |
| AGRONOMIC TRAITS | | | | | | |
| Stay Green (at 65 days after anthesis) (rate on scale from 1 = worst to 9 = excellent) | 7 | | | 7 | | |
| % Dropped Ears (at 65 days after anthesis) | 0 | | | 0 | | |
| % Pre-anthesis Brittle snapping | 0 | | | 0 | | |
| % Pre-anthesis Root Lodging | 0 | | | 3 | | |
| % Post-anthesis Root Lodging (at 65 days after anthesis) | 0 | | | 0 | | |
| Kg/ha Yield of Inbred Per Se (at 12–13% grain moisture) | | | | | | |

In interpreting the foregoing color designations, reference may be made to the Munsell Glossy Book of Colr, a standard color reference. Color codes: 1. light green, 2. medium green, 3. dark green, 4. very dark green, 5. green-yellow, 6. pale yellow, 7. yellow, 8. yellow-orange, 9. salmon, 10. pink-orange, 11. pink, 12. light red, 13 cherry red. 14. red, 15. red and white, 16. pale purple, 17. purple, 18. colorless, 19. white, 20. white capped, 21. buff, 22. tan, 23. brown, 24. bronze, 25. variegated, 26. other.

Comments:
1) Heat Units per day were calculated using the standard formula: HU={MaxTemp (86)+Min Temp (50)]/2−50.
2) Data for this exhibit was collected at London, Ontario, Canada, MN and WI.
3) Large standard deviations are probably due to environmental factors at each individual location where the variety was observed. Since the varieties reported in this exhibit are inbreds, the response to the environment is probably more pronounced than a hybrid or a combination of these inbred lines. Any stress at specific times during the growing season could influence results.
4) The anther of NP2315 appears to have a slight pale purple shade, whereas this coloring is absent in A619.
5) Glume bars of NP2315 and A619 are green/yellow, whereas some glume bars of A619 have a pale purple shade.
6) The silk color of NP2315 is green/yellow (2.5GY 8/8) with pale purple shaded ends (5RP 5/6).
7) The Disease and Insect Ratings were taken in MN in 2001 and 2002.

The invention also encompasses plants of inbred maize line NP2315 and parts thereof further comprising one or more specific, single gene traits which have been introgressed into inbred maize line NP2315 from another maize line. Preferably, one or more new traits are transferred to inbred maize line NP2315, or, alternatively, one or more traits of inbred maize line NP2315 are altered or substituted. The transfer (or introgression) of the trait(s) into inbred maize line NP2315 is for example achieved by recurrent selection breeding, for example by backcrossing. In this case, inbred maize line NP2315 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172–175; Fehr (1987) Principles of Cultivar Development, Vol. 1: Theory and Technique, 360–376).

The laboratory-based techniques described above, in particular RFLP and SSR, are routinely used in such backcrosses to identify the progenies having the highest degree of genetic identity with the recurrent parent. This permits to accelerate the production of inbred maize lines having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity is based on molecular markers used in the laboratory-based techniques described above. Such molecular markers are for example those known in the art and described in Boppenmaier, et al., "Comparisons among strains of inbreds for RFLPs", Maize Genetics Cooperative Newsletter (1991) 65, pg. 90, or those available from the University of Missouri database and the Brookhaven laboratory database. The last backcross generation is then selfed to give pure breeding progeny for the gene(s) being transferred. The resulting plants have essentially all of the morphological and physiological characteristics of inbred maize line NP2315, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

Many traits have been identified that are not regularly selected for in the development of a new inbred but that can be improved by backcrossing techniques or genetic transformation. Examples of traits transferred to inbred maize line NP2315 include, but are not limited to, waxy starch, herbicide tolerance, resistance for bacterial, fungal, or viral disease, insect resistance, enhanced nutritional quality, improved performance in an industrial process, altered reproductive capability, such as male sterility or male fertility, yield stability and yield enhancement. Other traits transferred to inbred maize line NP2315 are for the production of commercially valuable enzymes or metabolites in plants of inbred maize line NP2315.

Traits transferred to maize inbred line NP2315 are naturally occurring maize traits, which are preferably introgressed into inbred maize line NP2315 by breeding methods such as backcrossing, or are heterologous transgenes, which are preferably first introduced into a maize line by genetic transformation using genetic engineering and transformation techniques well known in the art, and then introgressed into inbred line NP2315. Alternatively a heterologous trait is directly introduced into inbred maize line NP2315 by genetic transformation. Heterologous, as used herein, means of different natural origin or represents a non-natural state. For example, if a host cell is transformed with a nucleotide sequence derived from another organism, particularly from another species, that nucleotide sequence is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory sequences. A transforming nucleotide sequence may comprise a heterologous coding sequence, or heterologous regulatory sequences. Alternatively, the transforming nucleotide sequence may be completely heterologous or may comprise any possible combination of heterologous and endogenous nucleic acid sequences.

A transgene introgressed into maize inbred line NP2315 typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements such as for example translation enhancers or termination signals. In a preferred embodiment, the nucleotide sequence is the coding sequence of a gene and is transcribed and translated into a protein. In another preferred embodiment, the nucleotide sequence encodes an antisense RNA, a sense RNA that is not translated or only partially translated, a t-RNA, a r-RNA or a sn-RNA.

Where more than one trait are introgressed into inbred maize line NP2315, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of inbred maize line NP2315 in addition to the multiple genes in the resulting maize inbred line. The genes responsible for a specific, single gene trait are generally inherited through the nucleus. Known exceptions are, e.g. the genes for male sterility, some of which are inherited cytoplasmically, but still act as single gene traits. In a preferred embodiment, a heterologous transgene to be transferred to maize inbred line NP2315 is integrated into the nuclear genome of the donor, non-recurrent parent. In another preferred embodiment, a heterologous transgene to be transferred to into maize inbred line NP2315 is integrated into the plastid genome of the donor, non-recurrent parent. In a preferred embodiment, a plastid transgene comprises one gene transcribed from a single promoter or two or more genes transcribed from a single promoter.

In a preferred embodiment, a transgene whose expression results or contributes to a desired trait to be transferred to maize inbred line NP2315 comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559–64). In another preferred embodiment, a transgene comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137–41). In a preferred embodiment, an insecticidal gene introduced into maize inbred line NP2315 is a Cry1Ab gene or a portion thereof, for example introgressed into maize inbred line NP2315 from a maize line comprising a Bt-11 event as described in U.S. Pat. No. 6,114,608, which is incorporated herein by reference, or from a maize line comprising a 176 event as described in Koziel et al. (1993) Biotechnology 11: 194–200. In yet another preferred embodiment, a transgene introgressed into maize inbred line NP2315 comprises a herbicide tolerance gene. For example, expression of an altered acetohydroxyacid synthase (AHAS) enzyme confers upon plants tolerance to various imidazolinone or sulfonamide herbicides (U.S. Pat. No. 4,761,373). In another preferred embodiment, a non-transgenic trait conferring tolerance to imidazolinones is introgressed into maize inbred line NP2315 (e.g a "IT" or "IR" trait). U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoximine. Also, expression of a *Streptomyces* bar gene encoding a phosphinothricin acetyl transferase in maize plants results in tolerance to the herbicide phosphinothricin or glufosinate (U.S. Pat. No. 5,489,520). U.S. Pat. No. 5,013,659, which is incorporated herein by reference, is directed to plants that express a mutant acetolactate synthase (ALS) that renders the plants resistant to inhibition by sulfonylurea herbicides. U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a tolerant protoporphyrinogen oxidase enzyme in plants (U.S. Pat. No. 5,767,373). Another trait transferred to inbred maize line NP2315 confers tolerance to an inhibitor of the enzyme hydroxyphenylpyruvate dioxygenase (HPPD) and transgenes conferring such trait are, for example, described in WO 9638567, WO 9802562, WO 9923886, WO 9925842, WO 9749816, WO 9804685 and WO 9904021. All issued patents referred to herein are, in their entirety, expressly incorporated herein by reference.

In a preferred embodiment, a transgene transferred to maize inbred line NP2315 comprises a gene conferring tolerance to a herbicide and at least another nucleotide sequence encoding another trait, such as for example, an insecticidal protein. Such combination of single gene traits is for example a Cry1Ab gene and a bar gene.

Specific transgenic events introgressed into maize inbred line NP2315 can be obtained through the list of Petitions of Nonregulated Status granted by APHIS as of 10-12-2000. For example, introgressed from glyphosate tolerant event GA21 (9709901p), glyphosate tolerant/Lepidopteran insect resistant event MON 802 (9631701p), Lepidopteran insect resistant event DBT418 (9629101p), male sterile event MS3 (9522801p), Lepidopteran insect resistant event Bt11 (9519501p), phosphinothricin tolerant event B16 (9514501p), Lepidopteran insect resistant event MON 80100 (9509301p), phosphinothricin tolerant events T14, T25 (9435701p), Lepidopteran insect resistant event 176 (9431901p).

The introgression of a Bt11 event into a maize line, such as maize inbred line NP2315, by backcrossing is exemplified in U.S. Pat. No. 6,114,608, and the present invention is directed to methods of introgressing a Bt11 event into maize inbred line NP2315 using for example the markers described in U.S. Pat. No. 6,114,608 and to resulting maize lines.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which does not have the desired herbicide tolerance characteristic, and only those plants that have the herbicide tolerance gene are used in the subsequent backcross. This process is then repeated for the additional backcross generations.

This invention also is directed to methods for producing a maize plant by crossing a first parent maize plant with a second parent maize plant wherein either the first or second parent maize plant is a maize plant of inbred line NP2315 or a maize plant of inbred line NP2315 further comprising one or more single gene traits. Further, both first and second parent maize plants can come from the inbred maize line NP2315 or an inbred maize plant of NP2315 further comprising one or more single gene traits. Thus, any such methods using the inbred maize line NP2315 or an inbred maize plant of NP2315 further comprising one or more single gene traits are part of this invention: selfing, backcrosses, hybrid production, crosses to populations, and the like. All plants produced using inbred maize line NP2315 or inbred maize plants of NP2315 further comprising one or more single gene traits as a parent are within the scope of this invention. Advantageously, inbred maize line NP2315 or inbred maize plants of NP2315 further comprising one or more single gene traits are used in crosses with other, different, maize inbreds to produce first generation (F1) maize hybrid seeds and plants with superior characteristics.

In a preferred embodiment, seeds of inbred maize line NP2315 or seeds of inbred maize plants of NP2315 further comprising one or more single gene traits are provided as an essentially homogeneous population of inbred corn seeds. Essentially homogeneous populations of inbred seed are those that consist essentially of the particular inbred seed, and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs. The population of inbred corn seeds of the invention is further particularly defined as being essentially free from hybrid seed. The inbred seed population may be separately grown to provide an essentially homogeneous population of plants of inbred maize line NP2315 or inbred maize plants of NP2315 further comprising one or more single gene traits.

As used herein, the term "plant" includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk, seeds and the like.

Duncan, Williams, Zehr, and Widholm, Planta (1985) 165:322–332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262–265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64–65 (1986), refers to somatic embryogenesis from glume callus cultures and B. V. Conger, et al., Plant Cell Reports, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture procedures of maize are described in Green and Rhodes, "Plant Regeneration in Tissue Culture of Maize," Maize for Biological Research (Plant Molecular Biology Association, Charlottesville, Va. 1982, at 367–372) and in Duncan, et al., "The Production of Callus Capable of Plant Regeneration from Immature Embryos of Numerous *Zea mays* Genotypes," 165 Planta 322–332 (1985). Thus, another aspect of this invention is to provide cells that upon growth and differentiation produce maize plants having the physiological and morphological characteristics of inbred maize line NP2315. In a preferred embodiment, cells of inbred maize line NP2315 are transformed genetically, for example with one or more genes described above, for example by using a transformation method described in U.S. Pat. No. 6,114,608, and transgenic plants of inbred maize line NP2315 are obtained and used for the production of hybrid maize plants.

Maize is used as human food, livestock feed, and as raw material in industry. Sweet corn kernels having a relative moisture of approximately 72% are consumed by humans and may be processed by canning or freezing. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of inbred maize line NP2315 or of inbred maize line NP2315 further comprising one or more single gene traits, the plant produced from the inbred seed, the hybrid maize plant produced from the crossing of the inbred, hybrid seed, and various parts of the hybrid maize plant can be utilized for human food, livestock feed, and as a raw material in industry.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

DEPOSIT

Applicants have made a deposit of at least 2500 seeds of Inbred Maize Line NP2315 with the American Type Culture Collection (ATCC), Manassas, Va., 20110-2209 U.S.A., ATCC Deposit No: PTA-4929. This deposit of the Inbred Maize Line NP2315 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of maize inbred line designated NP2315, representative seed of said line having been deposited under ATCC Accession No: PTA-4929.

2. A maize plant, or a part thereof, produced by growing the seed of claim 1.

3. Pollen of the plant of claim 2.

4. An ovule of the plant of claim 2.

5. A maize plant, or a part thereof, having all the physiological and morphological characteristics of the plant according to claim 2.

6. The maize plant, or a part thereof, produced from the maize plant according to claim 2 or 5, by transformation with a transgene that confers upon said maize plant or a part thereof tolerance to an herbicide.

7. A maize plant according to claim 6, wherein said herbicide is glyphosate, gluphosinate, a sulfonylurea herbicide an imidazolinone herbicide, a hydroxyphenylpyruvate dioxygenase inhibitor or a protoporphyrinogen oxidase inhibitor.

8. A maize plant or a part thereof produced by transforming the maize plant according to claim 2 or 5 with a transgene that confers upon said maize plant or a part thereof, male sterility, insect resistance, disease resistance, bacterial resistance, fungal resistance or viral resistance.

9. The maize plant according to claim 8, wherein said transgene is *Bacillus thuringiensis* Cry1Ab gene.

10. The maize plant according to claim 8, wherein said transgene further comprises a bar gene.

11. A tissue culture of regenerable cells produced from themaize plant according to claim 2.

12. The tissue culture according to claim 11, wherein the regenerable cells are from a tissue selected from the group consisting of embryo, meristem, pollen, leave, anther, root, root tip, silk, flower, kernel, ear, cob, husk and stalk.

13. A maize plant regenerated from the tissue culture of claim 11 or 12, wherein the regenerated plant has all of the morphological and physiological characteristics of maize plant of inbred line NP2315, seed of said line having been deposited under ATCC Accession No: PTA-4929.

14. A method for producing maize seed comprising crossing a first parent maize plant with a second parent maize plant and harvesting the resultant maize seed, wherein said first or second parent maize plant is the inbred maize plant of claim 2.

15. The method according to claim 14, wherein the inbred maize plant is the female parent.

16. The method according to claim 14, wherein the inbred maize plant is the male parent.

* * * * *